United States Patent

Hirschberg et al.

Patent Number: 6,085,118
Date of Patent: Jul. 4, 2000

[54] IMPLANTABLE MULTI-ELECTRODE DEVICE FOR ELECTRICALLY STIMULATING A PHYSIOLOGICAL FUNCTION WITH AUTOMATIC SELECTION OF HOUSING TERMINAL-TO-ELECTRODE CONNECTION DEPENDENT ON A SENSED SIGNAL

[75] Inventors: Jakub Hirschberg, Täby; Hans Strandberg, Sundbyberg, both of Sweden

[73] Assignee: Pacesetter AB, Järfälla, Sweden

[21] Appl. No.: 09/214,997

[22] PCT Filed: Jul. 4, 1997

[86] PCT No.: PCT/SE97/01238

§ 371 Date: May 17, 1999

§ 102(e) Date: May 17, 1999

[87] PCT Pub. No.: WO98/03223

PCT Pub. Date: Jan. 29, 1998

[30] Foreign Application Priority Data

Jul. 23, 1996 [SE] Sweden .................................. 9602846

[51] Int. Cl.[7] ...................................................... A61N 1/36
[52] U.S. Cl. .................................................................. 607/9
[58] Field of Search ............................. 607/9, 15, 27, 607/28, 37

[56] References Cited

U.S. PATENT DOCUMENTS

| | | |
|---|---|---|
| 4,248,238 | 2/1981 | Joseph . |
| 4,628,934 | 12/1986 | Pohndorf et al. . |
| 5,423,873 | 6/1995 | Neubauer et al. . |
| 5,584,865 | 12/1996 | Hirschberg et al. . |

FOREIGN PATENT DOCUMENTS

| | | |
|---|---|---|
| 0 030 897 | 5/1981 | European Pat. Off. . |
| 0 598 617 | 5/1994 | European Pat. Off. . |
| 2 026 870 | 2/1980 | United Kingdom . |

*Primary Examiner*—Scott M. Getzow
*Attorney, Agent, or Firm*—Hill & Simpson

[57] ABSTRACT

An implantable cardiac stimulator has a connector with at least two terminals, each terminal being connectible to an implantable electrode for delivering stimulation pulses to a heart and/or for sensing cardiac activity signals. The stimulator also has a switch and a control unit which operates the switch, so that one or both terminals are connectible to the pulse generator and/or to an input stage. The control unit identifies a position status for at least one of the electrodes in response to a signal received by the input stage at the time of implantation of the stimulator. The control unit also can select a terminal to be connected to the pulse generator, dependent on the established position status.

16 Claims, 5 Drawing Sheets

IMPLANTABLE MULTI-ELECTRODE DEVICE FOR ELECTRICALLY STIMULATING A PHYSIOLOGICAL FUNCTION WITH AUTOMATIC SELECTION OF HOUSING TERMINAL-TO-ELECTRODE CONNECTION DEPENDENT ON A SENSED SIGNAL

TECHNICAL FIELD OF THE INVENTION

This invention relates to a system for electrical stimulation of physiologic function and, more particularly to electronic circuitry associated with cardiac stimulators for detecting intracorporal cardiac signals and providing stimulation signals.

DESCRIPTION OF RELATED ART

A cardiac pacemaker may include one or many electrode leads, each comprising one or many electrodes. During operation of the pacemaker said electrodes are coupled to electronic circuitry for sensing and pacing functions. A pacing output in the pacemaker may be coupled to a certain electrode such as a distal tip electrode positioned in the ventricle, and a sensing input may be coupled to another electrode such as a proximal ring electrode positioned in the ventricle. Accordingly the pacemaker may function to sense electrical impulses in the ventricle and to provide stimulation signals to the ventricle.

U.S. Pat. No. 4,628,934 discloses pacing and sensing circuitry provided in a sealed case, and coupled to electrodes via a reduction switch unit. By means of the reduction switch unit, which is provided outside of the sealed case, the number of feedthroughs from the electrodes to the pacing and sensing circuitry is reduced. According to one version of the disclosure the reduction switch selects one out of four electrodes, and according to other versions the reduction switch provides 2 to 4 or 2 to 8 selection. Selection is performed in response to a control signal.

U.S. Pat. No. 5,423,873 discloses a device of the type generally described in U.S. Pat. No. 4,628,934 in which the number of feedthroughs is further reduced by superimposing the control signal on the stimulation signal at the output of the pacing circuitry.

U.S. Pat. No. 4,248,238 discloses a heart pacing apparatus including a signal input, a signal output and two electrodes which are implanted in predetermined positions in a heart. A magnetically actuated switch means is used to selectively connect one electrode, having a first predetermined position, to the signal input and the other electrode, having a second predetermined position, to the signal output or vice versa.

In United Kingdom Specification 2 026 870 (Page 6, lines 27–42) different combination of leads (or conductors of leads) are selected in response to a detected failure (e.g., breakage of damage of a lead). This can be detected by loss of capture, i.e. failure to note a heart activity signal, or by measuring a high impedance between conductors.

European Application 0 598 617 discloses a device wherein a physician may program, using conventional programming techniques, into the device's memory the lead type and the placement of the lead (see e.g. abstract). The stored information, the polarity control signals, are then used to select predetermined electrodes and predetermined therapy in response of sensed heart signals (col. 3, lines 8–45). The positions of the different electrodes are already known (set by the physician) when a predetermined electrode is selected and connected to e.g. an output circuit.

SUMMARY OF THE INVENTION

An object of the invention is to provide an implantable stimulator having at least two terminals to which electrodes are connectable while eliminating the need to connect the first electrode to a first predetermined terminal and the second electrode to a second predetermined terminal.

The above object is achieved in accordance with the invention in a stimulator wherein any electrode may be connected to any terminal of the stimulator. the inventive stimulator has a connector system having at least two terminals, each terminal being connectable to an implantable electrode for applying pulses to a heart and/or for sensing signals, a switch, and means for controlling the switch such that each terminal is selectably coupled to a pulse generator and/or to a sensor signal evaluator. According to the invention the control means is devised to establish a position status for at least one of the terminals in response to a signal received at the sensor signal evaluator in connection with the implantation of the stimulator unit. The generated status indicates the position of the electrode connected to the terminal. The control means is devised to select a terminal to be coupled to the pulse generator in response to the position status, and to cause the switch to couple the selected terminal to the pulse generator.

This solution has the advantage of eliminating the need for designation labels at the terminals of the implantable stimulator unit. Thus there is no need to provide labels instructing the surgery staff as to which lead is to be connected to which terminal. Furthermore, and perhaps more importantly, the inventive solution has the advantageous effect of eliminating the need to mate each electrode lead with a predetermined corresponding connector socket at the time of implantation. Thereby the duration of the surgical operation can be shortened.

According to a preferred embodiment the control switch is devised to cause the switch to consecutively couple the sensor signal evaluator to each terminal, and to record a signal value received by the sensor means for each terminal. The control means is also devised to establish a status value for at least one of the terminals in response to the recorded signal values.

According to one embodiment the sensor signal evaluator is devised to measure said received signal as an amplitude between a predetermined indifferent electrode and the terminal to which the switch couples the sensor signal evaluator. The housing of the implantable stimulator may act as the predetermined indifferent electrode.

According to one embodiment the control means is devised to establish the position status for a first connected electrode and for a second connected electrode in response to a combination of sensed signals, the signal combination including a first signal sensed by the first electrode and a second signal sensed by the second electrode. When, for example, a first electrode has been implanted in the atrium and a second electrode has been implanted in the ventricle the time interval between corresponding, or similar, signals detected by the first and the second electrode, respectively, provides information as to which electrode is positioned in the atrium and which electrode is positioned in the ventricle.

The claimed control means is illustrated in the examples below by a microprocessor co-operating with a read only memory, ROM, and with a control unit.

DESCRIPTION OF THE PREFERRED EMBODIMENTS

Figure 1:
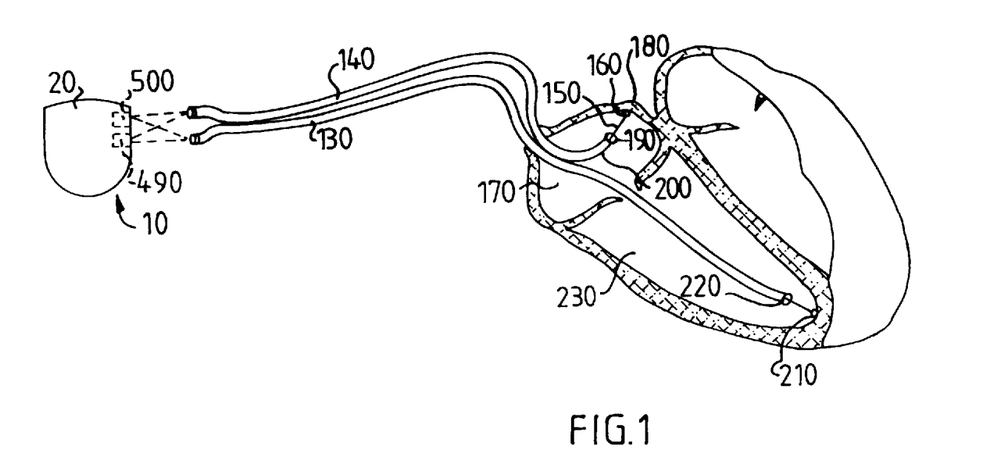
FIG. 1 shows a schematic representation of a dual chamber cardiac pacemaker shown implanted in association with a heart for pacing.

Referring to FIG. 1, there is shown a simplified representation of one way that an implanted pacemaker 10 may make electrical contact with the heart of a patient. FIG. 1 depicts the use of two bipolar leads 130 and 140, each being directed into a separate chamber of the right side of the heart. A bipolar electrode lead comprises two electrically insulated conductors. For example the lead 140 includes a first conductor 150 that is electrically connected to a distal tip electrode 160 of the lead. This distal tip electrode is typically placed in a cavity of the right atrium 170 referred to as the atrial appendage 180. A known distance from the distal tip 160 an electrode ring 190 is electrically connected to the other conductor 200 of the bipolar lead 140. Similarly a distal tip electrode 210 and a conductive ring electrode 220 are associated with the bipolar lead 130 that is placed in the apex of the right ventricle 230. The manner in which the leads 130 and 140 are inserted into the heart, as well as the manner in which the pacemaker 10 is implanted in the body of a patient, are well known in the art.

Figures 2A, 2B:
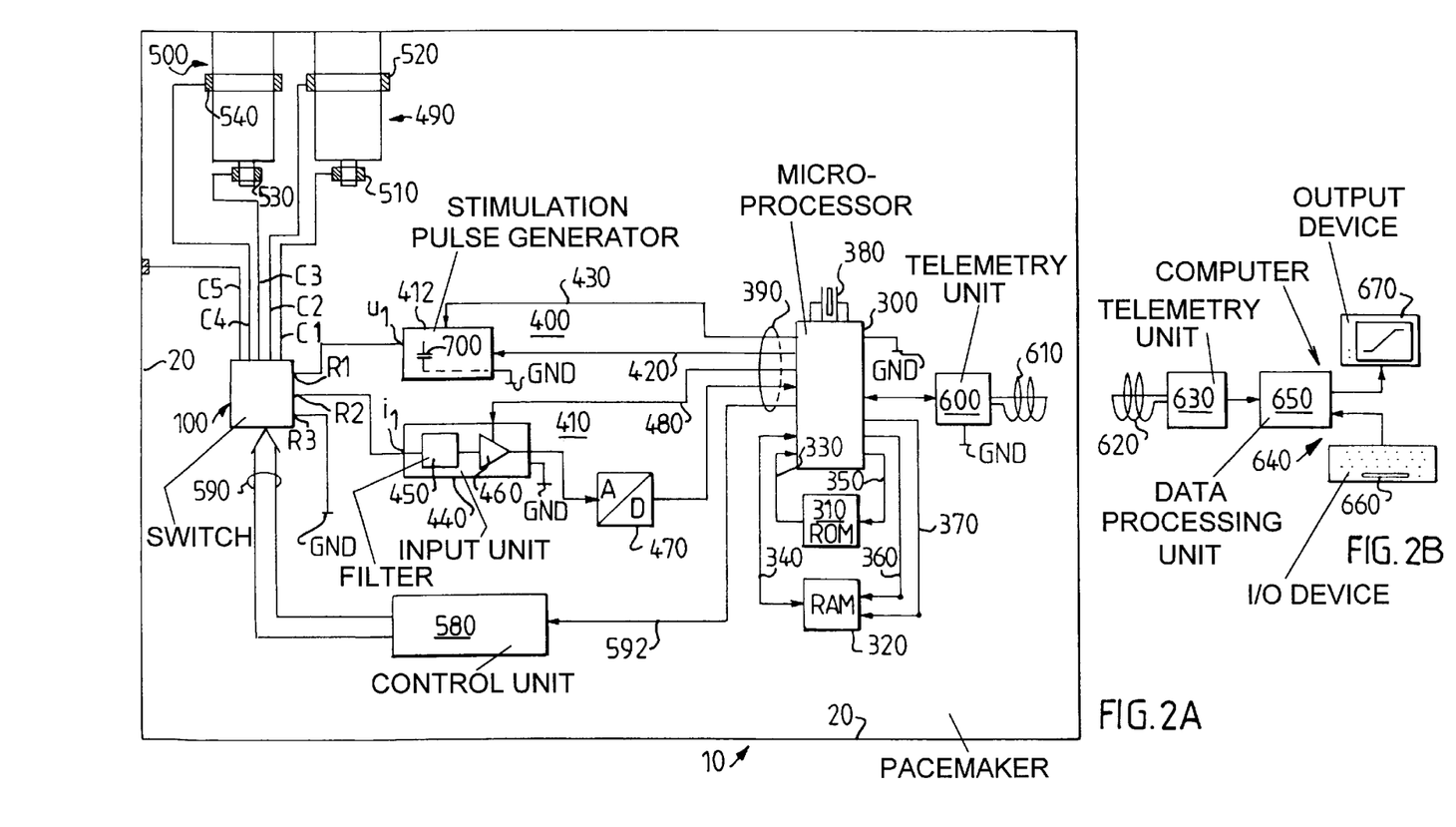
FIG. 2A shows a schematic block diagram of a first embodiment of a pacemaker according to the invention.
FIG. 2B shows an extracorporal signal-processing device adapted to be able to communicate with the pacemaker according to FIG. 2A.

A block diagram of a pacemaker body including electronic circuitry in accordance with the present invention is shown in FIG. 2A. The pacemaker 10 comprises a hermetically sealed housing 20. The pacemaker includes among other things a microprocessor 300 which is coupled to a read only memory, ROM, 310 and a read/write-memory, RAM, 320 via data busses 330, 340 and address busses 350, 360. There is also a lead 370 from the microprocessor 300 to the RAM 320 for setting the RAM 320 in a selected write mode or a selected read mode. A data program is stored in the ROM 310, and by means of this program the function of the pacemaker 10 is controlled. When, in the following, it is stated that the microprocessor 300 executes a certain function it is to be understood that the microprocessor executes a certain part of the program stored in the memory 310 using data stored in the memory 320.

A clock signal generator 380 provides a clock signal to the microprocessor and also thereby provides a time reference for the pacemaker. The microprocessor 300 has a number of input/output terminals 390 coupled to two signal channels 400, 410. The channel 400 is an output channel suitable for providing stimulation pulses to the heart. The channel 400 includes a stimulation pulse generator 412 having an output $U_1$. The pulse generator 412 is coupled to a corresponding output from the microprocessor 300 via a conductor 420, and the pulse generator 412 is arranged to produce a stimulation pulse in response to a signal provided from the output of the microprocessor. Digital data for determining for example the shape of the stimulation pulse, such as the amplitude and the duration, are provided to the pulse generator 412 via a lead 430 from the microprocessor 300.

The channel 410 includes a signal input unit 440 having an input $I_1$ for receiving an electrical signal corresponding to heart activity. The input unit 440 contains a filter 450 and an amplifier 460. The output of the amplifier 460 is coupled to an A/D converter 470. The output of the A/D converter provides digital data which are provided to a corresponding input of the microprocessor 300. The microprocessor 300 may control the amplification factor of the amplifier 460 by providing digital control data to the amplifier via a lead 480. The input channel 410 is devised to deliver information to the microprocessor about the amplitude of any received signal.

The invention, however, is not limited to the use of a microprocessor. The functions described in connection with the the microprocessor may alternatively be executed by other electronic circuits, such as for example random logic circuits.

The pacemaker 10 has a first connector having two sockets 490, 500 for mating with a corresponding second connector provided at one end of an implantable lead, such as the above described lead 130 and/or 140.

The socket 490 has a pin socket 510 and a connector ring 520, and the socket 500 has a pin socket 530 and a connector ring 540.

Figures 3, 5, 6:
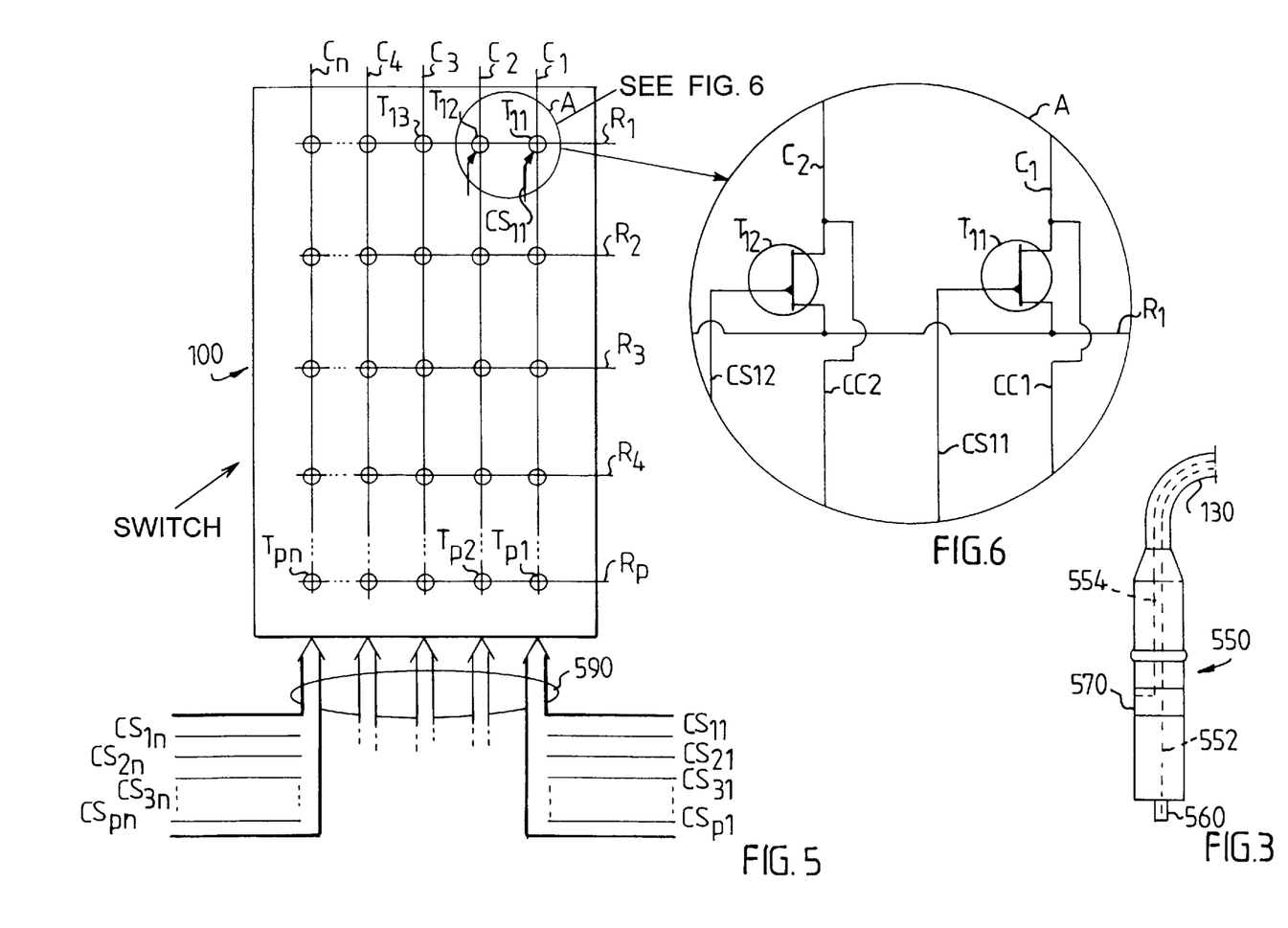
FIG. 3 shows an embodiment of a lead provided with a plug connector.
FIG. 5 is a schematic representation of a switch means according to one embodiment of the invention.
FIG. 6 is a detailed schematic of a part of the switch means according to FIG. 4.

FIG. 3 shows an embodiment of a plug connector 550 suitable for mating with one of the sockets 490, 500. The plug connector 550 may be a part of the above described lead 130 (FIG. 1), having two conductors 552, 554 for electrically interconnecting the distal tip electrode 210 with a pin terminal 560 and for connecting the ring electrode 220 with a ring terminal 570, respectively.

Referring again to FIG. 2A the pacemaker 10 also contains a switch 100 having first terminals $R_1$, $R_2$ and $R_3$ and second terminals $C_1$–$C_5$. The second terminal $C_1$ is coupled to pin socket 510, $C_2$ is coupled to connector ring 520, terminal $C_3$ is coupled to pin socket 530, terminal $C_4$ is coupled to connector ring 540, and terminal $C_5$ is coupled to the conductive housing 20, which is adapted to make contact with body tissue after implantation.

The first terminal $R_1$ of the switch 9 means 100 is coupled to the above described output $U_1$ of signal generator 410. The terminal $R_2$ is coupled to the input $I_1$ of input unit 440. The terminal $R_3$ is connected to signal ground. When, in the following, it is stated that a voltage signal has an amplitude, it is to be understood that the amplitude is the deviation from the potential at signal ground GND.

It is to be noted that the electronic circuitry 300, 600, 400, 410 may all be coupled to signal ground as illustrated in FIG. 2A. The housing 20, however, is not necessarily connected to signal ground. By means of the switch 100 the housing may be connected to any one of output $U_1$ or input $I_1$ or to signal ground. Alternatively the housing 20 may be disconnected from signal ground.

The switch 100 comprises switch units for selectively connecting each first terminal $R_1$, $R_2$, $R_3$ with an individual second terminal $C_1$, $C_2$, $C_3$, $C_4$, $C_5$ respectively, in response to a selection control signal provided to the switch 100 by a control unit 580 via a data bus 590. The control unit generates the selection control signal in response to a signal provided on an output lead 592 from the processor 300.

The microprocessor 300 is coupled to a telemetric device 600 capable of transmitting and receiving data. The telemetric device 600 has an antenna 610 for communicating with a corresponding extracorporal telemetric device.

FIG. 2B shows an extracorporal data processing arrangement having an antenna 620 coupled to a telemetric device 630 for enabling communication with an implanted telemetric device such as the above described device 600. The telemetric device 630 is coupled to a computer unit 640 having a data processing unit 650, an input/output device 660, such as a keyboard, and an output device 670 such as a screen.

When the device 10 is implanted the surgery staff will insert plug connectors of the type shown in FIG. 3 into the sockets 490 and 500.

In a specific example one of the plug connectors is associated with lead 140 having two electrodes 190 and 160, which have been placed in the atrium, while the other plug connector is associated with lead 130 having electrodes 210 and 220 which have been placed in the ventricle (see FIG. 1).

The surgery staff may insert any of the plug connectors in any one of the female connectors 490, 500, as indicated by the dashed lines in FIG. 1.

Hence, referring to FIGS. 1, 2A and 3, electrode 160 being positioned in the atrium may become connected either to terminal $C_1$ or to terminal $C_3$ of the switch 100. Similarly electrode 210 may be connected to either one of terminals $C_3$ or $C_1$. Any of the the electrodes 160, 190, 210 and 220 may make contact with body tissue in the heart and thereby they are capable of picking up electrical signals. Such electrical signals may come from spontaneous biological activity.

The stimulator is devised to establish when it has been implanted and to establish the position status for the electrodes connected to the stimulator after implantation. In other words the stimulator is devised to determine what part of the body the implanted electrode makes contact with in connection with the implantation of the stimulator and/or the electrode.

In order to establish the position status the microprocessor in cooperation with the control unit 580, causes the switch 100 to consecutively couple the sensor terminal $R_2$ to each terminal $C_1$ to $C_4$, while keeping the ground terminal $R_3$ coupled to the housing 20.

The microprocessor in this manner causes the switch 100 to sample the signal potentials at each terminal C1–C4, and in a coordinated manner each sample value is recorded in the memory 320.

The sample frequency is chosen such that the temporal progression of each signal from terminals $C_1$–$C_4$, and hence from the electrodes 210, 220, 160 and 190, are recorded (FIG. 2A and FIG. 1).

When, as in the present example shown in FIG. 1, two electrodes are placed in the atrium and two other electrodes are placed in the ventricle the above described sampling procedure will lead to four sampled signals, each indicating the depolarization and repolarization signature of spontaneous heart signals. The electrodes 210 and 220 placed in the ventricle will, however, deliver signals having the depolarization signature with a phase lag as compared to the signals picked up by the atrial electrodes 160 and 190.

Figure 7A:
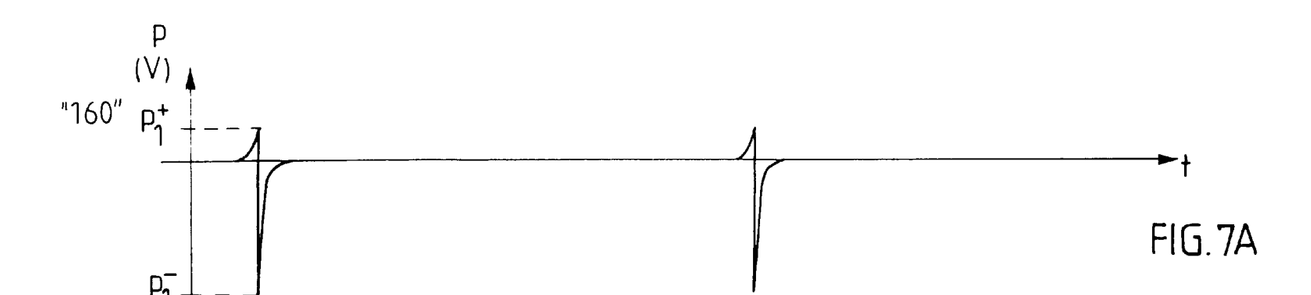
FIGS. 7A and 7B illustrate a depolarization signal sensed by an electrode in an atrium and in a ventricle, respectively.
Figure 7B:
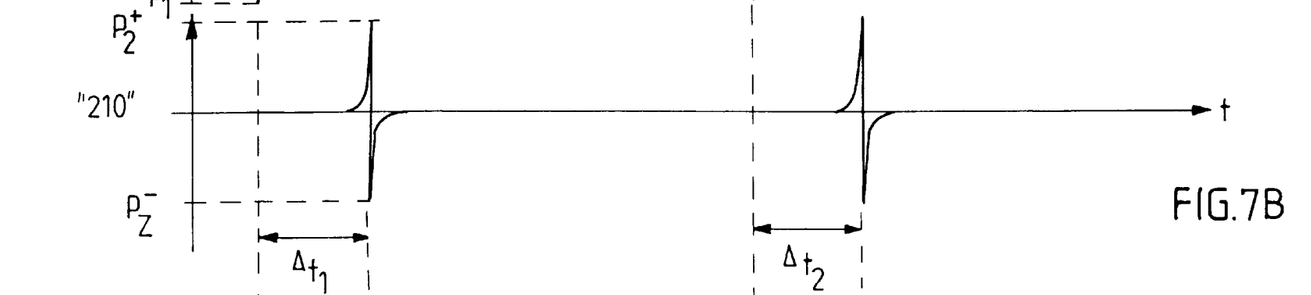

FIGS. 7A and 7B illustrate the depolarization signature recorded by an electrode in an atrium and a ventricle, respectively. In FIG. 7B the reference $At_1$ indicates the time difference between a registration of a depolarization wave by an atrial electrode, such as 160 in FIG. 1, and the registration of the corresponding depolarization wave by a ventricular electrode, such as 210 in FIG. 1.

Depending on the electrode position in relation to the sinoatrial node and the atrioventrincular node, respectively the duration from the generation of a signal by the sinoatrial node to the registration of the signal by the electrode will differ. The microprocessor functions to measure the time difference $\Delta t$ a predetermined number of times, and calculates a mean value of the measured values to $\Delta t_1$–$\Delta t_n$.

The number of $\Delta t$-values measured are in an interval from 3 to 50, preferably between 5 and 15.

After having recorded the input signals for a sufficient time, the microprocessor in accordance with the program is devised to compare the recorded signals with prerecorded signals or signal information so as to identify the shape of the signal, such as the depolarization/repolarization signature of heart activity.

The microprocessor also compares magnitude of the positive voltage $P^+$ with the magnitude of the negative voltage $P^-$ in order to establish the position of the corresponding electrode. As illustrated in FIG. 7A as compared to FIG. 7B the relation between these magnitudes are different between atrial and ventricular depolarization signatures.

Figure 7C:
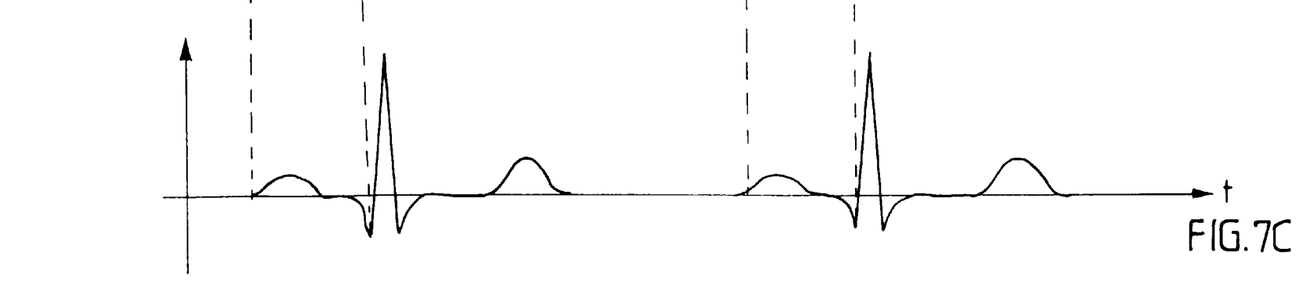
FIG. 7C illustrates a surface ECG.

FIG. 7C illustrates a surface ECG and the vertical dashed lines in FIGS. 7A–7C illustrates the temporal relation between the signals shown in FIGS. 7A–7C.

As mentioned above, the microprocessor in accordance with the program is devised to mutually compare the recorded signal so as to identify any phase lag between the recorded signals. Having identified the depolarization/repolarization signatures of the signals picked up by electrodes 160 and 210, and having identified the phase lag between the occurance of the signatures, the microprocessor concludes which of terminals C1/510 and C3/530 is connected to electrode 160 and 210, respectively.

Referring to FIGS. 1 and 2A, if lead 130 is connected to socket 500 and lead 140 is connected to socket 490, the microprocessor will conclude that terminal C3/530 is connected to a ventricle electrode, and that terminal C1/510 is connected to an atrial electrode.

The microprocessor generates status information indicating the positional conclusions, and records this status information in the memory 320.

In accordance with a predefined decision support information, recorded in the memory 310 or in memory 320, the microprocessor selects to couple the pulse generator terminal $V_1/R$ to one of the atrial electrodes 160 or 190. In the above example this means that terminal C1/510 or C2/520 is coupled to output terminal $U_1/R_1$ for the purpose of delivering stimulation signals to the atrium.

In a manner similar to that of the microprocessor, the switch sampling of the signal potentials at each terminal, the identification of the depolarization/repolarization signatures of the signals, identification of the phase lag between the occurance of the signatures, and the conclusion drawn as to which of the terminals is connected to which electrode may instead be performed by the extracorporal data processing arrangement 620,630,640,650,660,670 in combination with an external ECG recording unit. The computer unit 640 may comprise programs for performing these tasks. Alternatively, the medical staff may control the computer unit 640 by means of the input/output device 660.

For the purpose of establishing whether the stimulator has been implanted, the stimulator may measure the impedance between the terminals for connecting to the electrodes. Prior to implantation the impedance is very high. After having connected implanted electrodes to the terminals 510–540 the impedance normally drops significantly. By providing a sensor function for detecting this impedance change the stimulator position status establishment is reliably activated at implantation.

The pulse generator 412 (FIG. 2A) may for example include a reservoir capacitor 700 which is charged to a predesignated stimulation voltage. By way of controlling the switch 100 to couple terminal $R_1$ to terminal $R_2$ the difference in capacitor voltage before and after stimulation may be established. This voltage difference corresponds to the electrode impedance. Thus the impedance can be established in a manner well known in the art, and described for example in European Application-0 572 799.

Alternatively the implantation may be detected in the following manner:

The microprocessor 300, in cooperation with the control unit 580, causes the switch 100B to consecutively couple the sensor terminal R2 to each terminal C1 to C4, while keeping the ground terminal R3 coupled to the housing 20. Hence the housing acts as a reference electrode 20 and any signal picked up by the electrodes and delivered to the terminals C1 to C4 can be related to the potential of the reference electrode 20. When input unit 410, 440 receives electrical signals the microprocessor operates to identify if any of the received signals correspond to heart activity (FIG. 2A). When a signal is identified to correspond to heart activity the microprocessor will start timer procedure for counting a predetermined time. The predetermined time is, for example, of a duration sufficient for allowing the surgery staff to complete the implantation.

Figure 4:
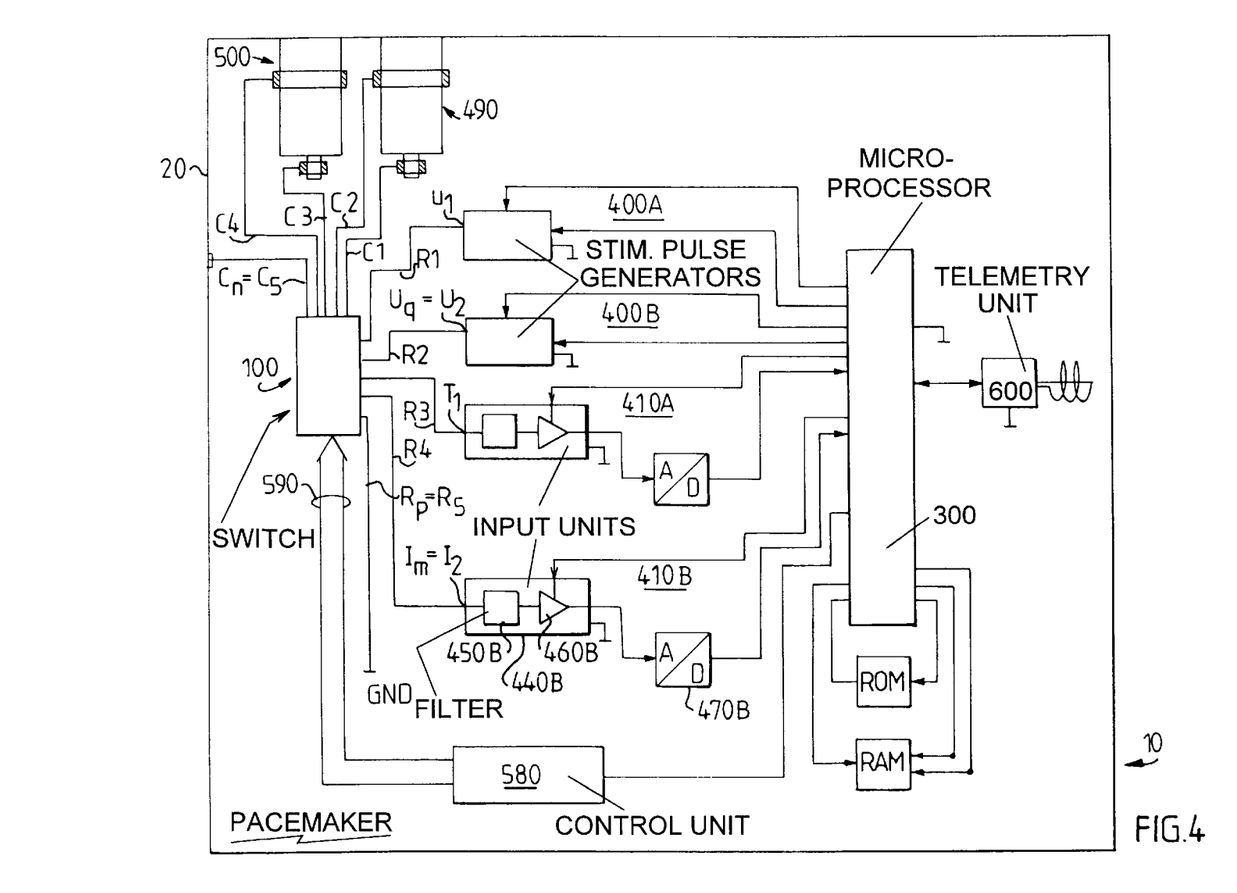
FIG. 4 shows a schematic block diagram of a second embodiment of a pacemaker according to the invention.

FIG. 4 shows a second embodiment of a stimulation device according to the invention. The second embodiment differs from the first embodiment in that two output channels 400A and 400B, and two input channels 410A, 410B are provided.

Furthermore the switching means 100 according to the second embodiment comprises five first terminals $R_1$–$R_5$ and five second terminals $C_1$–$C_5$. The second terminals $C_1$–$C_5$ are coupled to the connector means 490, 500 and to the housing 20 in the same manner as described in connection with FIG. 2A above. The number of signal channels 400, 410 are not, however, limited to the above exemplified numbers. There may, according to the invention, be another number of input channels 410 and/or output channels 400.

FIG. 5 is a schematic representation of a switch 100 according to one embodiment of the invention.

The switch, 100 has a number of first terminals $R_1$, $R_2$ . . . $R_p$ for coupling to input channels $I_1$–$I_m$ and output channels $U_1$–$U_q$ as shown in FIGS. 1, 2A and 5. One of the first terminals $R_1$–$R_p$ may be connected to signal ground.

According to one version of the invention the number p of first terminals equals the number of signal channels and signal ground terminals:

$$p=m+q+1$$

According to another version of the invention the housing 20 of the pacemaker is permanently coupled to signal ground GND and consequently the number of first terminals can be reduced to p=m+q. As mentioned above the switching means comprises a number of second terminals $C_1$–$C_n$ which, when the device 10 is implanted into the body of a patent, are connected to electrodes for making contact with body tissue.

In FIG. 5 the switch 100 is illustrated as a matrix having row terminals $R_1$–$R_p$ and column terminals $C_1$–$C_n$. Each of the p·n positions of the matrix comprises a switch unit T. The switch unit $T_{11}$ has a closed state in which it connects the row terminal $R_1$ with the column terminal $C_1$, and an open state in which the row terminal $R_1$ is disconnected from the column terminal $C_1$. Similarly switch unit $T_{12}$ connects or disconnects row terminal $R_1$ and column terminal $C_2$. Generally speaking switch unit $T_{uv}$ connects or disconnects first terminal $R_u$ and second terminal $C_v$, where $2 \leq u \leq p$ and $2 \leq v \leq n$.

Each switch unit $T_{uv}$ is controllable in response to an individual control signal $CS_{uv}$. The control signals are provided to the switch units via the signal bus 590.

FIG. 6 illustrates an enlarged part A of the switch 100. Row terminal $R_1$ is via a lead coupled to the source terminal of a Field Effect Transistor (FET), acting as switch unit $T_{11}$. Terminal $R_1$ is also coupled to the source terminal or drain terminal of transistors $T_{12}$–$T_{1n}$.

Similarly terminal $C_1$ is coupled to the drain terminal of FET $T_{11}$, as well as to drain or source of transistors $T_{11}$–$T_{p1}$.

The gate terminal of FET $T_{11}$ is via a lead coupled to a corresponding signal line in control bus 590 for receiving a control signal $CS_{11}$. The control signal $CS_{11}$ may be used for controlling the state of FET $T_{11}$ between a conductive low impedance state and a substantially non-conductive state.

As noted, an embodiment of a pacemaker includes a sensor circuit that looks for electrical signals from spontaneous heart activity. On detection of such activity, the pacemaker is devised to establish a position status value indicating the implanted position of at least one electrode in response to the signals registered by the electrode. The analysis of the registered signals may be based on electrical signals coming from purely spontaneous biological activity picked up by electrodes in a heart or in other parts of a subjects body.

Alternatively the implantable device 10 may be devised to deliver an electrical signal to one electrode while sensing signals from one or several of the other electrodes. A comparative analysis of the shape and timing of the sensed signal with that of the delivered signal, enables conclusions as to the position of the electrode, since the sensed signal will be influenced by the body in dependence thereon. This influence may be the manner in which the electrical signal propagates in the actual body tissue, or the body tissue may, in response to a signal delivered signal delivered by the stimulator, be stimulated to perform a certain biological activity which is detectable.

According to one embodiment of the invention the implantable stimulator unit is devised to measure the impedance between one or several of the terminals $C_1$–$C_5$ and ground. When, for example, terminal $C_1$ is connected to an atrial electrode and the housing 20 acts as signal ground an impedance measurement between terminals $C_1$ and $C_5$ indicates the impedance between the atrial electrode and the housing 20.

By measuring the impedances for the terminals $C_1$–$C_5$ continously or by sampling them sufficiently often to achieve the temporal progression of the impedances, the stimulator unit can obtain an impedance curve for each terminal $C_1$–$C_5$. The impedance measured from an electrode implanted in or near a heart varies in accordance with the mechanical work of the heart. This variation pattern depends on whether or not the electrode is implanted in a heart, and it is even possible to discern in which heart chamber the electrode is positioned. The manner in which impedance may be measured is well known in the art. The stimulator may also be devised to establish the position status for the terminals by a combination of the above manners.

According to another embodiment of the invention an implantable signal sensor device may be connected between two of the terminals 510, 520, 530 and 540. The signal sensor device may be for example a piezo-electric sensor for measuring pressure or acceleration. Such a sensor device has specific electrical properties which can be identified. The implantable stimulator unit 10 is devised to recognize these properties and to establish status information indicating whether and to which terminals 510, 520, 530 and 540 such a sensor device is connected. Another example of an implantable sensor device connectable to the connector means 490 or 500 is a red light oxygen sensor. Such a sensor includes a diode, which has a specific electric characteristic in for example a certain voltage drop in one direction.

According to yet another embodiment of the invention the microprocessor 300 establishes the position status for the electrodes and delivers this status information to the telemetric device 600 for transmission to the extracorporal computer 640 (FIGS. 2A and 2B). The computer 640 is provided with software for directing the dataprocessing unit 650 to generate terminal selection information indicating the terminal to be coupled to the pulse generator in response to the status information. The dataprocessing unit 650 thereafter delivers the terminal selection information to the telemetric device 630 for transmission to the telemetric device 600 in the implanted stimulator 10. On reception of, and in response to, the terminal selection information the microprocessor 300 operates to cause the switch 100 to couple the selected terminal to the pulse generator.

According to another embodiment of the invention the microprocessor 300 is devised to cause the switch means to consecutively couple the input means to at least two terminals 510, 520, 530, 540 in connection with the implantation of the stimulator.

The microprocessor 300 is devised to record a signal value received by the input means for each terminal and the stimulator is adapted to to transmit the recorded signal values to the extracorporal unit via the telemetric devices 600, 630. The extracorporal computer 640 is devised to establish a position status for at least one of the terminals (510, 520, 530, 540) in response to the received signals, to select a terminal to be coupled to the pulse generator in response to the position status, and to transmit the selection information to the stimulator. In response to the terminal selection information the microprocessor 300 operates to cause the switch 100 to couple the selected terminal to the pulse generator.

What is claimed is:

1. An implantable cardiac stimulator comprising:
   an implantable housing;
   a pulse generator in said housing which emits stimulation pulses;
   a connector at said housing having two terminals;
   two implantable leads respectively connected to said two terminals, each of said leads carrying an electrode adapted for implantation in a heart at an intracardiac position;
   an input stage for sensing cardiac activity;
   a control unit connected to said input stage;
   a switch connected to said two terminals and to said pulse generator and to said input stage for initially connecting one of said two terminals to said input stage, said input stage sensing cardiac activity from the electrode of the lead connected to the terminal connected to the input stage and supplying a signal corresponding to said cardiac activity to said control unit; and
   said control unit comprising means for determining a position status, including identification of the intracardiac position of the electrode of the lead connected to the terminal connected to the input stage, and for controlling said switch to selectively connect one of said two terminals to said pulse generator dependent on said position status.

2. An implantable cardiac stimulator as claimed in claim 1 wherein said control means comprises means for operating said switch to successively connect each of said two terminals to said input stage, said input stage sensing the respective cardiac activity from each of said electrodes and supplying first and second signals, respectively corresponding to the respective cardiac activity from said electrodes, to said control unit, and said control unit comprising means for determining a first position status from said first signal and a second position status from said second signal, and for selectively connecting one of said two terminals to said pulse generator dependent on said first position status and said second position status.

3. An implantable cardiac stimulator as claimed in claim 1 further comprising means in said housing for detecting connection of one of said electrodes to one of said terminals and for thereupon causing said control unit to initiate determination of said position status.

4. An implantable cardiac stimulator as claimed in claim 1, wherein said control means comprises means for measuring an amplitude of said signal and for determining said position status dependent on said amplitude.

5. An implantable cardiac stimulator as claimed in claim 1 wherein said control means comprises means for measuring a positive amplitude value and a negative amplitude value of said signal, and for determining said position status dependent on a relation between said position amplitude value and said negative amplitude value.

6. An implantable cardiac stimulator as claimed in claim 1 wherein said control means comprises means for identifying a chronological progression of said signal and for determining said position status dependent on said chronological progression.

7. An implantable cardiac stimulator as claimed in claim 1 wherein both of said two terminals have a lead connected thereto and wherein said input stage generates a first cardiac activity signal from a first of said electrodes simultaneously with a second cardiac signal from a second of said electrodes, and wherein said control means comprises means for determining said position status from a combination of said first cardiac activity signal and said second cardiac activity signal.

8. An implantable cardiac stimulator as claimed in claim 1 further comprising an indifferent electrode and means for selectively connecting said indifferent electrode to said control unit, and wherein said control unit comprises means for determining said position status from a signal between said indifferent electrode and the electrode of the lead connected to the terminal connected to the input stage.

9. An implantable cardiac stimulator as claimed in claim 1 further comprising an indifferent electrode and means for connecting said indifferent electrode to said control unit, and wherein said control unit comprises means for determining said position status from a signal between said indifferent electrode and the electrode of the lead connected to the terminal connected to the input stage.

10. An implantable cardiac stimulator as claimed in claim 9 wherein said housing comprises said indifferent electrode.

11. An implantable cardiac stimulator as claimed in claim 1 further comprising an indifferent electrode, and wherein said control unit operates said switch to successively connect each of said two terminals to said input stage so that said input stage has a first electrode and a second electrode connected thereto, and wherein said control unit comprises means for measuring a first impedance between said first electrode and said indifferent electrode and for measuring a second impedance between said second electrode and said indifferent electrode, and for determining said position status dependent on said first impedance and said second impedance.

12. An implantable cardiac stimulator as claimed in claim 11 wherein said housing comprises said indifferent electrode.

13. An implantable cardiac stimulator as claimed in claim 1 further comprising an indifferent electrode, and wherein said control unit comprises means for identifying a chronological variation of an impedance between the electrode of the lead connected to the terminal connected to the input unit and said indifferent electrode, and for determining said position status dependent on said chronological variation of said impedance.

14. An implantable cardiac stimulator as claimed in claim 13 wherein said housing comprises said indifferent electrode.

15. An implantable cardiac stimulator as claimed in claim 1 wherein said control unit operates said switch to connect each of said terminals to said input stage, said input stage generating the first signal corresponding to cardiac activity from a first of said electrodes and a second signal corresponding to cardiac activity from a second of said electrodes, and wherein said control unit comprises means for identifying a first position status from said first signal and a second position status from said second signal, and for operating said switch to connect said pulse generator and said input stage to a selected one of said terminals dependent on said first position status and second position status.

16. An implantable cardiac stimulator as claimed in claim 1 further comprising an implantable physiological signal generator for generating a sensor signal, said input stage comprising a sensor signal evaluation unit connected to said physiological signal generator via said connector, said input stage supplying a signal corresponding cardiac activity, derived at least in part from said sensor signal, to said control unit.

* * * * *